(12) United States Patent
Benfer et al.

(10) Patent No.: US 7,009,198 B2
(45) Date of Patent: Mar. 7, 2006

(54) PATTERN METHOD AND SYSTEM FOR DETECTING FOREIGN OBJECT DEBRIS USING A FLUORESCENT DRILLING LUBRICANT

(75) Inventors: Greg L. Benfer, St. Charles, MO (US); Daniel E. Wagoner, Florissant, MO (US); Michael L. Taylor, Collinsville, IL (US); John D. Fitts, St. Charles, MO (US); John C. Clayton, Ste. Genevieve, MO (US); Lynn E. Johnson, Warrenton, MO (US)

(73) Assignee: The Boeing Company, Chicago, IL (US)

( * ) Notice: Subject to any disclaimer, the term of this patent is extended or adjusted under 35 U.S.C. 154(b) by 205 days.

(21) Appl. No.: 10/720,628

(22) Filed: Nov. 24, 2003

(65) Prior Publication Data

US 2004/0113071 A1    Jun. 17, 2004

Related U.S. Application Data

(63) Continuation-in-part of application No. 09/954,404, filed on Sep. 17, 2001.

(51) Int. Cl.
   *G01N 21/88*  (2006.01)
(52) U.S. Cl. ............... 250/559.4; 250/302; 250/336.1; 250/372; 175/42; 184/6.4
(58) Field of Classification Search ............ 250/559.4, 250/559.41, 336.1, 372, 302; 173/DIG. 3; 175/17, 42; 184/6.4; 356/237.1; 324/553; 340/631
See application file for complete search history.

(56) References Cited

U.S. PATENT DOCUMENTS

| 4,787,990 | A | | 11/1988 | Boyd ........................ 175/42 |
| 5,225,675 | A | * | 7/1993 | O'Donnell .................. 250/302 |
| 5,667,840 | A | * | 9/1997 | Tingey et al. ................. 427/8 |
| 5,807,605 | A | * | 9/1998 | Tingey et al. ................. 427/8 |
| 6,749,772 | B1 | * | 6/2004 | Zumdome ............. 252/301.34 |

* cited by examiner

*Primary Examiner*—David Porta
*Assistant Examiner*—Stephen Yam
(74) *Attorney, Agent, or Firm*—Artz & Artz, P.C.

(57) ABSTRACT

A method of detecting a non-fixed object created during hole drilling operations on a system (12) includes applying a light emitting lubricant (25) to a drill bit (37) of a hole-drilling device (31). The light emitting lubricant adheres to foreign object debris 10 that is created during the hole drilling operations. The foreign object debris 10 can include shavings (29), portions of the drill bit (37), or the entire drill bit (37). The objects are illuminated with an object illuminator (16). At least one of the objects (10) is determined to be a nonmember within a known pattern of objects and is identified to be a non-fixed object in response to illumination of the objects.

25 Claims, 2 Drawing Sheets

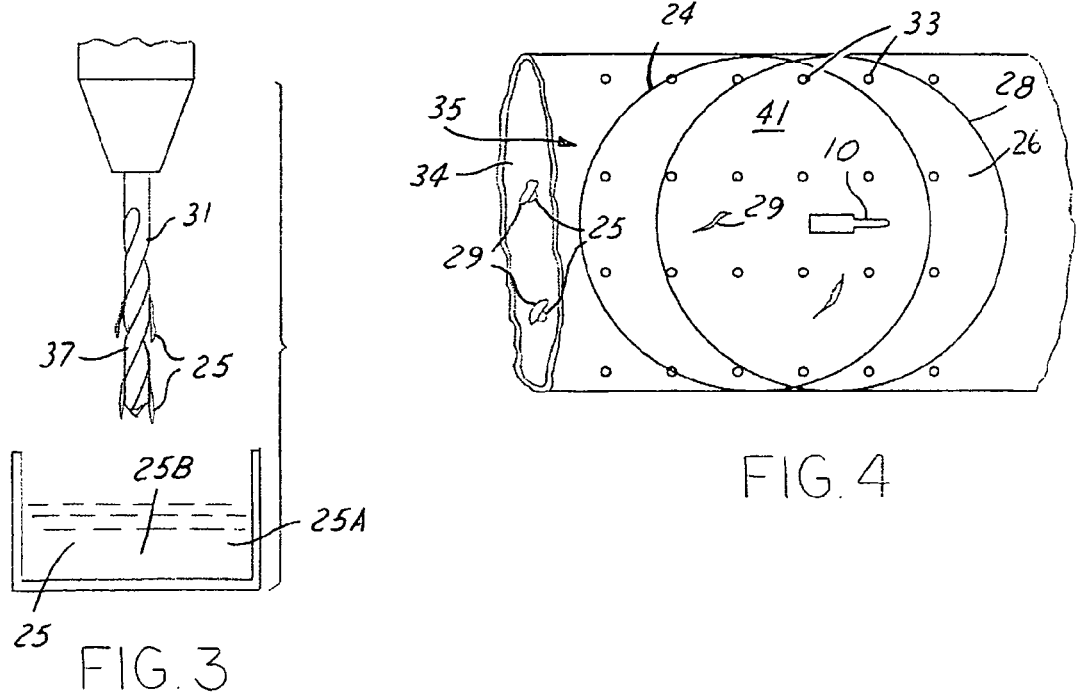
FIG. 3
FIG. 4
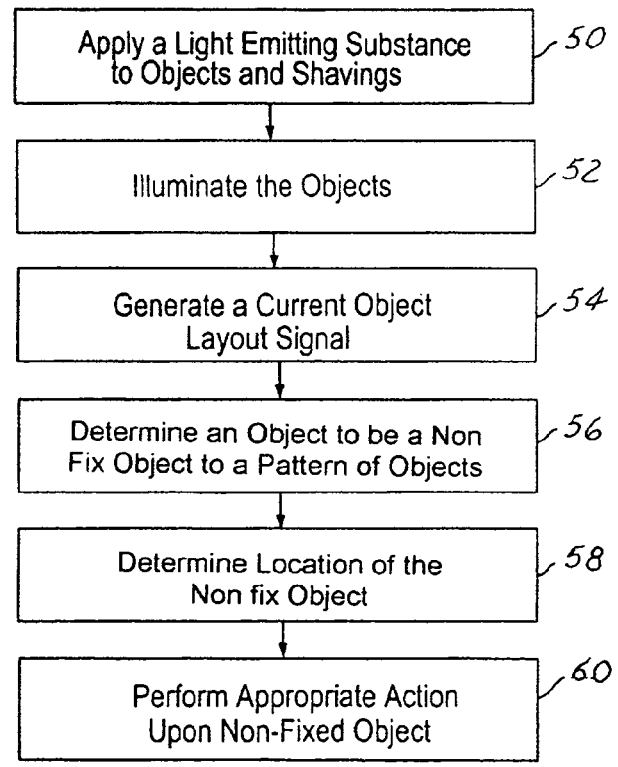
FIG. 5

PATTERN METHOD AND SYSTEM FOR DETECTING FOREIGN OBJECT DEBRIS USING A FLUORESCENT DRILLING LUBRICANT

RELATED APPLICATION

The present application is a continuation-in-part (CIP) application of U.S. patent application Ser. No. 09/954,404 filed Sep. 17, 2001 entitled "A Method for Detecting Foreign Object Debris", which is incorporated by reference herein.

TECHNICAL FIELD

The present invention relates generally to object detection methods, and more particularly to a method and system for detecting foreign object debris created during drilling operations using a fluorescent lubricant.

BACKGROUND OF THE INVENTION

Aircraft safety is an ongoing concern for aircraft producers. An unknown loose object on board an aircraft may cause an aircraft to malfunction or not operate as designed. Unknown loose objects are referred to as foreign object debris (FOD) in the art.

FOD are difficult to detect and many hours of searching an aircraft for FOD occur during production of an aircraft, to assure the aircraft is free from loose objects, before the aircraft leaves a production facility or is operated. Moreover, because the detection of FOD relies almost solely on visual inspection, it can be subject to human error.

FOD are of various size and shape and can go undetected in large aircraft. A large aircraft has various cavities, pockets, and crevices that cause the process of detecting FOD to be difficult. For example, a small FOD item, such as a metal shaving or drill bit, lying in a dark crevice may go undetected during the search of a large aircraft. These metal shavings and drill bits may cause damage to wires and tubing. As one of ordinary skill thus appreciates, the more the amount of undetected FOD, the more the likelihood exists of an aircraft system malfunctioning.

A current method exists for locating a component that requires a supplemental restraining device on a portion of a gas turbine engine, as described in Garrity U.S. Pat. No. 6,150,656 entitled "Method of Assembly and Inspection for a Gas Turbine Engine", hereinafter referred to as Garrity. In Garrity, a fluorescent material is applied to components of a gas turbine engine that require a supplemental restraining device before assembly thereof. An electromagnetic radiation is directed at the gas turbine engine to illuminate the fluorescent material. Upon illumination of the fluorescent material, a confirmation is made as to whether the components that requires a supplemental restraining device do in fact have a supplemental restraining device properly installed. As known in the art and as taught by Garrity, in order to properly install a supplemental restraining device, such as a lock-wire, to a component, the component must be fixed otherwise the supplemental restraining device does not serve its intended purpose.

One known method of detecting foreign object debris is described in Wagoner et al., U.S. Patent Application entitled "A Method for Detecting Foreign Object Debris", hereinafter referred to as Wagoner. Wagoner teaches a method of detecting a non-fixed object, such as a fastener, within an aircraft. A light emitting substance is applied to the non-fixed object. A non-fixed object illuminator is used to illuminate the light emitting substance. The non-fixed object is detected due to the illumination of the light emitting substance.

In both Wagner and Garrity above, the light emitting substance is directly applied to the non-fixed object prior to any manufacturing or assembly steps. However, FOD is also created during the manufacturing and assembly of aircraft. For example, FOD in the form of metal shavings is created during hole drilling operations. These metal shavings could be a portion of the drilled substrate or could be portions of the deteriorating drill bits. Drill bits and metal shavings are hard to detect and can be sharp, potentially causing damage to wires and tubings.

Thus, it is highly desirable to easily detect and remove FOD created during hole drilling operations.

SUMMARY OF THE INVENTION

The foregoing and other advantages are provided by a method of detecting a non-fixed object in a system. The method includes introducing a light emitting substance to the composition of a lubricant used in hole drilling operations, specifically on aircraft.

The lubricant adheres to FOD that is created during hole drilling operations. The light emitting substance of the lubricant coated FOD is then illuminated with an object illuminator. This allows the lubricant coated FOD to be removed prior to placing the aircraft or other manufactured device within operation.

To ensure that all FOD created during hole drilling operations is coated with enough lubricant to be detectable, it is necessary to ensure that the hole drilling equipment is properly lubricated during each and every hole drilling operation. As such, the lubricant is added at regular intervals to the hole drilling equipment.

In accordance with the above and other advantages of the present invention, production costs of an aircraft are reduced. Costs are reduced directly due to decreased time and energy necessary in searching for non-fixed objects, including metal shavings. Costs are also reduced indirectly as a result of potential decreases in post manufacturing costs due to aircraft malfunction caused by non-fixed objects going undetected.

The present invention itself, together with attendant advantages, will be best understood by reference to the following detailed description, taken in conjunction with the accompanying figures.

BRIEF DESCRIPTION OF THE DRAWINGS

For a more complete understanding of this invention reference should now be had to the embodiments illustrated in greater detail in the accompanying figures and described below by way of examples of the invention wherein:

FIG. 3 illustrates a hole drilling device having a drill bit coated with a lubricant according to one preferred embodiment of the present invention;

FIG. 4 is a representative illustration of a non-member object being detected on the surface or beneath the surface of a portion of the substrate of FIG. 1; and FIG. 5 is a flow chart illustrating the method of FIG. 1 in accordance with a preferred embodiment of the present invention.

DETAILED DESCRIPTION OF THE PREFERRED EMBODIMENT

While the present invention is described with respect to a method and system for detecting shavings created during hole drilling operations during the manufacture and assembly of an aircraft, the present invention may be adapted to be used for a variety of other components and systems including automotive vehicles, electronic or mechanical systems, machinery, or other components or systems that may require detection of a the non-fixed shavings. The present invention may also be used in various production and manufacturing processes including before, during, and after assembly of a system. In the following description, various operating parameters and components are described for one constructed embodiment. These specific parameters and components are included as examples and are not meant to be limiting.

Figure 1:
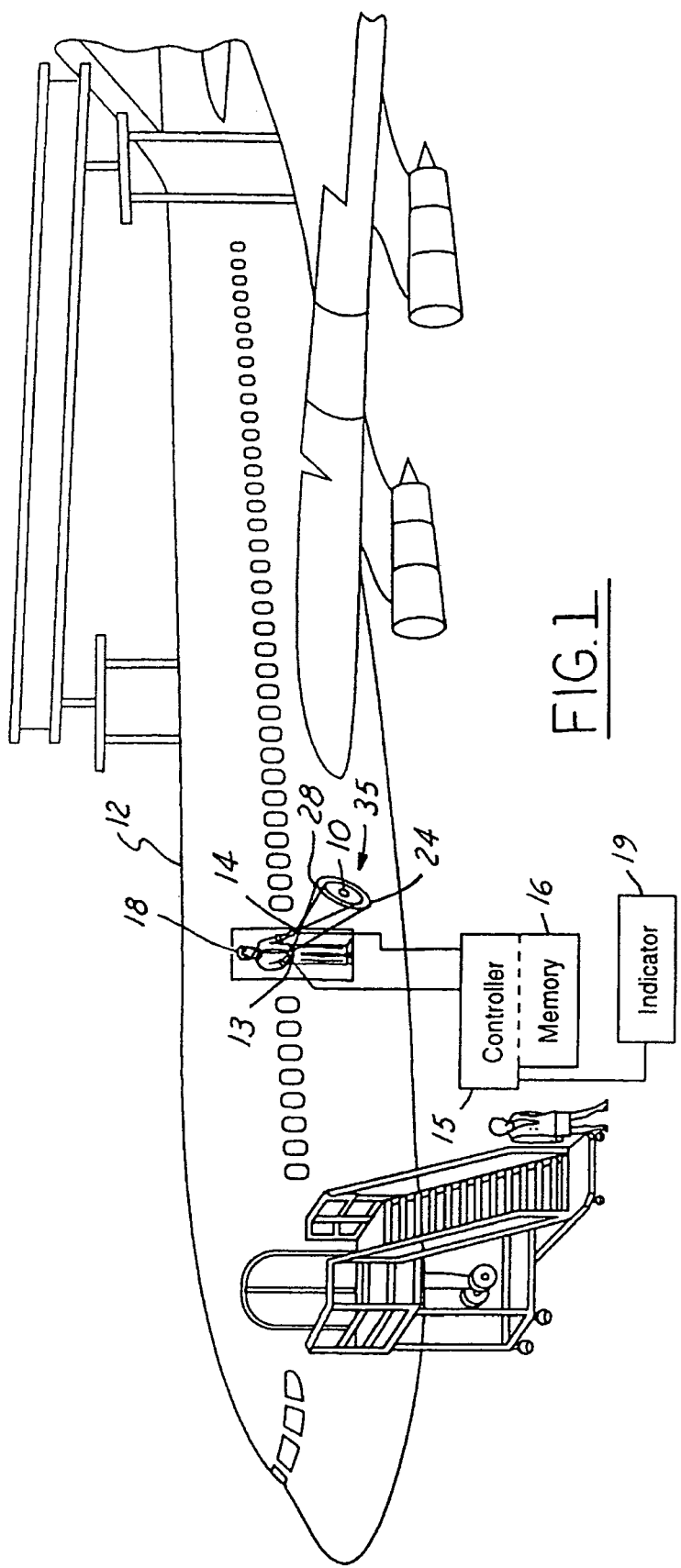
FIG. 1 is a representative illustration of implementing a method of detecting a non-fixed object in an aircraft using a foreign object debris detection system in accordance with a preferred embodiment of the present invention.

Referring now to FIG. 1, a representative illustration of implementing a method of detecting a non-fixed object 10 in an aircraft 12 using a foreign object debris (FOD) detection system in accordance with an embodiment of the present invention is shown. The non-fixed object 10 consists essentially of metal shavings (shown as 29 on FIGS. 2 and 3) or other associated debris created during hole drilling operations that are performed during manufacture and assembly of the aircraft 12. The non-fixed object 10 may also be, for example, a tool, a system object, a non-system object, a loose or free moving object, a chip, or other non-fixed object. A non-fixed object refers to an object that is loose or not fixed to the aircraft 12.

The system includes an object illuminator 13, a pattern detector 14, and a controller 15 having a memory 16. The object illuminator 13 illuminates the object 10. Reflected illuminance from the object 10 is detected by the detector 14. The controller 15 determines the object 10 to be a nonmember of a known pattern of objects. The object 10 may be determined to be FOD by the controller 15 or by the operator 18. An indicator 19 may be electrically coupled to the controller 15 and indicate that the object 10 is a nonmember to a known pattern of objects.

The illuminator 13 may be any of the following: an ultraviolet light (black light), a fluorescent light, or a white light. The object illuminator 13 may be operated manually by the operator 18 or through the use of the controller 15 or an automated machine. The object illuminator 13 is powered as to illuminate areas throughout the aircraft 12 as to determine that an object is a nonmember of a known pattern of objects.

The pattern detector 14 may detect fluorescent, phosphorescent, luminescent, incandescent, photoluminescent, hotoluminescent, or other light emission known in the art. The pattern detector 14 may be infrared-based, photoilluminescent-based, or be of some other form of light detector known in the art.

The controller 15 is preferably a microprocessor-based controller such as a computer having a central processing unit, memory (RAM and/or ROM), and associated input and output buses.

The indicator 19 may be used to signal or indicate a nonmember identification signal in response to the object detection signals. The indicator 19 may generate video or audio signals, be as simple as an LED, may be in the form of a display, or may be some other type of indicator known in the art. The indicator 19 may simply indicate that FOD is present-or may specify type and location of the FOD.

The illuminator 13, the pattern detector 14, the controller 15, and the indicator 19 may be integrally form into a single device or may be stand alone devices, as shown.

Figure 2:
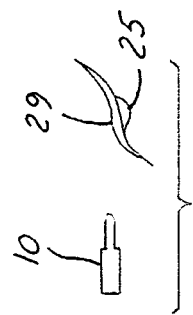
FIG. 2 is a representative illustration of a nonmember shaving on the aircraft in accordance with a preferred embodiment of the present invention.

Referring now also to FIG. 2, representative illustration of a nonmember object 10 of a pattern of objects 20 on the aircraft 12 in accordance with a preferred embodiment of the present invention is shown. The nonmember object 10 is at least partially coated with a lubricant 25 having a light emitting substance that is capable of being detected by the operator 18 using the object illuminator 13.

As best shown in FIG. 4, the non-member object 10 is created during a hole drilling process and consists primarily of shavings 29 created as a hole-drilling device 31 creates a hole 33 within a substrate 35. For example, the hole 33 may be created in the wing of an aircraft. The shavings 29 consist of portions of the substrate 35 and/or portions of the drill bit 37. These shavings 29 fall within the interior region 34 of the substrate 35 or on the outer surface 41 of the substrate 35 and are not easily detected by the human eye.

As best shown in FIG. 3, the hole-drilling device 31 may consist of any conventional type apparatus that has enough power (torque) to easily drill a hole through the substrate 35. The drill bits 37 are conventional as well, and are selected based on the type and thickness of the substrate 35.

To ensure that the shavings 29 may be easily found and removed from the system prior to final assembly, a lubricant 25 having a light emitting substance 25A is introduced to the drill bit 37 prior to the drilling of the holes 33. Preferably, the drill bit 37 is dipped within the lubricant 25 at regular intervals. For example, the drill bit 37 is preferably dipped in the lubricant 25 on a regular basis to ensure that each shaving 29 is coated with enough lubricant 25 to be detectable.

The lubricant 25 preferably comprises a mixture of a drilling fluid 25A and a light emitting substance 25B. The drilling fluid 25A is typically a water-based or oil-based drilling fluid used in medium and heavy duty machining operations. For example, one preferred oil-based drilling fluid 25A is Acculube LB-2000 metalworking lubricant, a high performance natural base oil available from ITW Fluid Products Group of Glenview, Ill.

The light emitting substance 25B is a material that is fluorescent, phosphorescent, luminescent, incandescent, photoluminescent, hotoluminescent, or otherwise light emitting. The light emitting substance 25B must be compatible with the drilling fluid 25A within which it is utilized. The light emitting substance 25B also must not substantially break down during the hole drilling process. One example of a light emitting substance 25B is DYX-163, a fluorescent dye from ITW Dymon-Dykem of Olathe, Kans.

The light emitting lubricant 25 can be formed by admixing the light emitting substance 25B to the drilling fluid to a uniform consistency. As one of ordinary skill appreciates, the amount of light emitting substance 25B added to the drilling fluid 25A is dependent upon numerous factors, including the compatibility of the light emitting substance within the drilling fluid 25A and also the light emitting properties of the light emitting substance 25B within the drilling fluid 25A. However, the light emitting properties of the light emitting substance 25B must be sufficient for an operator to easily detect the partially coated shavings 29. For example, between about 0.5 and 5, and more preferably about 2 weight percent, DYX-163 fluorescent dye is added to about 95 to 99.5 weight percent Acculube LB-2000 to form one preferred light emitting lubricant.

One preferred commercially available light emitting lubricant 25 that meets these criteria is Acculube LB-2000 Fluorescent (ALX-06) metalworking lubricant, available from ITW Fluid Products Group of Glenview, Ill.

Once the shavings 29 has been subjected to the lubricant 25, as indicated generally by reference numeral 50, they can be detected the detector 14 or by the operator 18. In accordance, with the preferred system, the operator 18 moves around the aircraft 12 with the object illuminator 13 to look for objects that are not fixed to the aircraft 12. The non-fixed object 10 is in a location 24 on the aircraft 12 near a drilling hole 33. The object illuminator 13 is operated in order to illuminate an area 26 of location 24. The illumination of the area 26 is represented by beam 28, in a close proximity and to illuminate the object 10.

In accordance with the method, at least a portion of the object 10 is illuminated as well as other nearby objects with the object illuminator 13, as generally indicated by reference number 52. The detector 14 in response to reflected light from illumination of the objects 10 generates a current object layout signal, as generally indicated by reference number 54. The current object layout signal contains illuminated object information such as object location, size, illuminance, and other object identification characteristics known in the art.

The object 10, and particularly the shavings 29, is determined to be a non-fixed object 10 within a known pattern of objects, by either the controller 15 or by the operator 18, in response to illumination thereof, as generally indicated by reference number 56. Known patterns may be stored within the memory 16. The patterns may consist of fixed object locations, relative distances between fixed object, and type and style of the fixed objects. When an object, such as the object 10, is not within a proper location, having the proper size, proper illuminance, or other object characteristic known in the art, the operator 18 or the controller 15 may determine the object to be FOD. The controller 15 may in response to the current object layout signal determine the object 10 to be a nonmember to the pattern 20 and generate a FOD signal, which is indicated by the indicator 19.

The operator 18 then determines the location of the non-member object, as generally indicated by reference numeral 58. The operator 18 then performs the appropriate action to the non-fixed object 10, as generally indicated by reference numeral 60. This includes removing the non-fixed object 10, fastening the non-fixed object 10 to the aircraft 12, performing some other task known in the art, or determining that no action needs to be performed on the non-fixed object 10. For example, shavings 29 or portions of the drill bit 37 created during the hole drilling process, are likely removed from the aircraft 12 prior to final assembly and delivery. In addition, drill bits 37 that inadvertently fall off the hole drilling device 31 during hole drilling operations may also be recovered.

The present invention provides an efficient and improved technique for detecting non-fixed objects within an aircraft. The technique is quick, easy, and inexpensive to perform. The technique saves costs involved in production and manufacturing of an aircraft and post manufacturing costs caused by component malfunctions due to undetected non-fixed object.

The above-described apparatus, to one skilled in the art, is capable of being adapted for various purposes and is not limited to the following systems: automotive vehicles, electronic or mechanical systems, machinery, or other components or systems that may require detection of a non-fixed object. The above-described invention may also be varied without deviating from the spirit and scope of the invention as contemplated by the following claims.

What is claimed is:

1. A method of detecting a shaving created during a hole drilling operation on a substrate of a system, the method comprising:
   forming a lubricant having a light emitting substance;
   applying said lubricant to a hole-drilling device;
   drilling a hole within the substrate using said hole drilling device, wherein the process of drilling said hole creates one or more shavings located on or within said system, wherein a portion of said lubricant adheres to each of said one or more shavings;
   illuminating the system with an object illuminator;
   identifying at least one non-fixed object within the system; and
   identifying said at least one non-fixed object to be one of said one or more shavings.

2. The method of claim 1 further comprising:
   determining whether to remove said one shaving from the system.

3. The method of claim 1 wherein identifying at least one non-fixed object within the system comprises determining at least one object to be a non-fixed object in a system from at least one of an automotive vehicle, a machine, an electronic system, and a mechanical system.

4. The method of claim 1, wherein forming the lubricant comprises:
   introducing a first amount of a drilling fluid with a second amount of a light emitting substance to a mixing device, wherein said second amount comprises between about 0.5 and 5 weight percent of the total weight of said first amount and said second amount; and
   mixing said first amount and said second amount to a uniform consistency.

5. The method of claim 4, wherein said drilling fluid comprises an oil-based drilling fluid.

6. The method of claim 4, wherein said drilling fluid comprises a water-based drilling fluid.

7. The method of claim 4, wherein said light emitting substance comprises a fluorescent dye.

8. The method of claim 1 further comprising reapplying said lubricant to said drill bit after every five hole drilling operations.

9. The method of claim 1 further comprising:
   drilling at least one more additional hole with said hole drilling device; and
   reapplying said lubricant to said hole-drilling device after drilling said at least one more additional hole.

10. A method of detecting a drill bit, or a portion of a drill bit, displaced from a hole drilling device during a hole drilling operation on a substrate of a system, the method comprising:
    forming a lubricant having a light emitting substance;
    applying said lubricant to the drill bit coupled to the hole-drilling device;
    drilling a hole within the substrate using the hole-drilling device, wherein the process of drilling said hole causes the drill bit or the portion of the drill bit to be displaced from the hole-drilling device, wherein a portion of said lubricant adheres to the drill bit or to the portion of the drill bit;
    illuminating the system with a object illuminator;

identifying at least one non-fixed object within the system; and identifying said at least one non-fixed object to be the drill bit or the portion of the drill bit.

11. The method of claim 10 further comprising:

determining whether to remove said the drill bit or portion of the drill bit from the system.

12. The method of claim 10 wherein identifying at least one non-fixed object within the system comprises determining at least one object to be a non-fixed object in a system from at least one of an automotive vehicle, a machine, an electronic system, and a mechanical system.

13. The method of claim 10, wherein forming the lubricant comprises:

introducing a first amount of a drilling fluid with a second amount of a light emitting substance to a mixing device, wherein said second amount comprises between about 0.5 and 5 weight percent of the total weight of said first amount and said second amount; and mixing said first amount and said second amount to a uniform consistency.

14. The method of claim 13, wherein said drilling fluid comprises an oil-based drilling fluid.

15. The method of claim 13, wherein said drilling fluid comprises a water-based drilling fluid.

16. The method of claim 13, wherein said light emitting substance comprises a fluorescent dye.

17. The method of claim 10 further comprising reapplying said lubricant to the drill bit after every five hole drilling operations.

18. The method of claim 1 further comprising:

drilling at least one more additional hole with the hole drilling device; and reapplying said lubricant to the hole-drilling device after drilling said at least one more additional hole.

19. A method for detecting and removing foreign object debris created during hole drilling operations in a system from at least one of an automotive vehicle, a machine, an electronic system, and a mechanical system, the method comprising:

providing a hole drilling device having a drill bit;

forming a light emitting lubricant having a light emitting substance;

introducing said light emitting lubricant to said hole drilling device;

drilling a hole within a substrate with said hole drilling device, wherein the process of drilling said hole creates foreign object debris at least partially coated with said light emitting lubricant, said foreign object debris selected from the group consisting of one or more shavings, one or more portions of said drill bit, and said drill bit;

illuminating the system with an object illuminator;

identifying at least one non-member object within the system; and identifying said at least one non-member object to be said foreign object debris;

determining whether to remove said foreign object debris; and removing said foreign object debris.

20. The method of claim 19, wherein forming the lubricant comprises:

introducing a first amount of a drilling fluid with a second amount of a light emitting substance to a mixing device, wherein said second amount comprises between about 0.5 and 5 weight percent of the total weight of said first amount and said second amount; and mixing said first amount and said second amount to a uniform consistency.

21. The method of claim 19, wherein said drilling fluid comprises an oil-based drilling fluid.

22. The method of claim 19, wherein said drilling fluid comprises a water-based drilling fluid.

23. The method of claim 20, wherein said oil-based drilling fluid comprises Acculube LB-2000 metalworking lubricant.

24. The method of claim 18 further comprising reapplying said light emitting lubricant to the drill bit after every five hole drilling operations.

25. The method of claim 10 further comprising:

drilling at least one more additional hole with said hole drilling device; and reapplying said lubricant to said hole-drilling device after drilling said at least one more additional hole.

* * * * *